United States Patent [19]

Trivedi

[11] Patent Number: 4,923,896
[45] Date of Patent: May 8, 1990

[54] N-(SUBSTITUTED ARYL)-N'-(SUBSTITUTED ALKOXY)-UREAS AND THIOUREAS AS ANTIHYPERCHOLESTEROLEMIC AND ANTIATHEROSCLEROTIC AGENTS

[75] Inventor: Bharat K. Trivedi, Canton, Mich.

[73] Assignee: Warner-Lambert Company, Morris Plains, N.J.

[21] Appl. No.: 308,911

[22] Filed: Feb. 9, 1989

[51] Int. Cl.$^5$ .................... A61K 31/21; C07C 83/10
[52] U.S. Cl. ................................. 514/507; 560/313
[58] Field of Search ................... 560/313; 514/507

[56] References Cited

U.S. PATENT DOCUMENTS 3,112,342  11/1963  Luckenbaugh .................... 560/313

*Primary Examiner*—Mary C. Lee
*Assistant Examiner*—Robert C. Whittenbaugh
*Attorney, Agent, or Firm*—Francis J. Tinney

[57] ABSTRACT

Novel N-[substituted aryl]-N'-(substituted alkoxy)-urea and thiourea derivatives are described, as well as methods for the preparation and pharmaceutical composition of same, which are useful in preventing the intestinal absorption of cholesterol and thus are useful in the treatment of hypercholesterolemia and atherosclerosis.

8 Claims, No Drawings

N-(SUBSTITUTED ARYL)-N'-(SUBSTITUTED ALKOXY)-UREAS AND THIOUREAS AS ANTIHYPERCHOLESTEROLEMIC AND ANTIATHEROSCLEROTIC AGENTS

BACKGROUND OF THE INVENTION

The present invention relates to novel N-[substituted aryl]-N'-(substituted alkoxy)-urea and thiourea derivatives useful as pharmaceutical agents, to methods for their production, to pharmaceutical compositions which include these compounds, and a pharmaceutically acceptable carrier, and to pharmaceutical methods of treatment. More particularly, the novel compounds of the present invention prevent the intestinal absorption of cholesterol in mammals by inhibiting the enzyme acyl-coenzyme A (Acyl-CoA):cholesterol acyltransferase (ACAT).

The atheromatous plaque, which is the characteristic lesion of atherosclerosis, results from deposition of plasma lipids, mainly cholesteryl esters, in the intima of the arterial wall. Progressive enlargement of the plaque leads to arterial constriction and ultimately coronary heart disease. A number of clinical trials have shown a causal relationship between hypercholesterolemia and coronary heart disease.

Agents that control dietary cholesterol absorption moderate serum cholesterol levels. Dietary cholesterol is absorbed from the intestinal lumen as free cholesterol which must be esterified with fatty acids. This reaction is catalyzed by the enzyme acyl-CoA: cholesterol acyltransferase (ACAT). The resulting cholesteryl esters are packaged into the chylomicrons which are secreted into the lymph. Inhibitors of ACAT not only prevent absorption of dietary cholesterol but also prevent the reabsorption of cholesterol which has been released into the intestine through endogenous regulatory mechanisms, thus lowering serum cholesterol levels and ultimately counteracting the formation or development of atherosclerosis.

Copending U.S. Ser. No. 147037, filed Feb. 5, 1988, now abandoned describes certain substituted urea, thiourea, carbamate, and thiocarbamate compounds as potent ACAT inhibitors.

Copending U.S. Ser. No. 176079, filed Mar. 30, 1988, pending, describes certain N-[(2,6-disubstituted)-phenyl]-N'-diarylalkyl]ureas as potent ACAT inhibitors.

Copending U.S. Ser. No. 175089, filed Mar. 30, 1988, pending describes certain N-[[2,6-disubstituted)phenyl]-N'-arylalkyl]ureas as potent ACAT inhibitors.

Copending U.S. Ser. No. 176080, filed Mar. 30, 1988, now U.S. Pat. No. 4,868,210 describes certain N-2,6-dialkyl or N-2,6-dialkoxyphenyl-N'-arylalkylurea compounds as potent ACAT inhibitors.

However, the compounds disclosed in the aforementioned copending United States applications do not suggest or disclose the combination of structural variations of the compounds of the present invention described hereinafter.

SUMMARY OF THE INVENTION

Accordingly, the present invention is a novel class of compounds of Formula I $$R-NH-\overset{\overset{X}{\|}}{C}-\underset{R_1}{N}-O-(CH_2)_n-R_2$$

wherein
R is phenyl,
phenyl mono or disubstituted with
  alkyl of from one to four carbon atoms,
  alkoxy of from one to four carbon atoms,
  fluorine,
  chlorine,
  bromine,
  iodine,
  $CO_2R_3$ wherein $R_3$ is alkyl of from one to four carbon atoms, or
  $NR_4R_5$ wherein $R_4$ and $R_5$ are independently hydrogen or alkyl of from one to four carbon atoms,
naphthyl, or
naphthyl substituted with alkyl of from one to four carbon atoms
  alkoxy of from one to four carbon atoms,
  fluorine,
  chlorine,
  bromine,
  iodine,
  $CO_2R_3$ wherein $R_3$ is as defined above, or
  $NR_4R_5$ wherein $R_4$ and $R_5$ are as defined above;
X is O or S;
$R_1$ is hydrogen,
alkyl of from four to eight carbon atoms, or phenylalkyl wherein alkyl is from one to four carbon atoms;
n is 0 or an integer of 1 or 2;
$R_2$ is bicyclo[2.2.1]heptane, bicyclo[2.2.2]octane, $$\underset{R}{\overset{}{\bigg\langle}}\overset{(CH_2)_{n'}}{\underset{}{\bigg\rangle}}$$

wherein n' is an integer of 2 to 6 and
R is as defined above, $$-\underset{R_8}{\overset{R_6}{\underset{|}{C}}}-R_7$$

wherein $R_6$ is hydrogen, alkyl of from one to eight carbon atoms or phenyl, $R_7$ is alkyl of from one to eight carbon atoms when $R_6$ is alkyl of from one to eight carbon atoms or $R_7$ is phenyl, and $R_8$ is phenyl or phenyl substituted with alkyl of from one to four carbon atoms, alkoxy of from one to four carbon atoms, fluorine, chlorine, bromine, iodine, $CO_2R_3$ wherein $R_3$ is as defined above, or $NR_4R_5$ wherein $R_4$ and $R_5$ are as defined above, wherein $R_9$ and $R_{10}$ are independently hydrogen, alkyl of from one to four carbon atoms, alkoxy of from one to four carbon atoms, fluorine, chlorine, bromine, iodine, $CO_2R_3$ wherein $R_3$ is as defined above or $NR_4R_5$ wherein $R_4$ and $R_5$ are as defined above, and A is 0, S, SO, $SO_2$, or —$CH_2$—, naphthyl or naphthyl substituted with alkyl of from one to four carbon atoms, alkoxy of from one to four carbon atoms,
fluorine,
chlorine,
bromine,
iodine,
$CO_2R_3$ wherein $R_3$ is as defined above, or
$NR_4R_5$ wherein $R_4$ and $R_5$ are as defined above; or a pharmaceutically acceptable acid addition salt thereof.

Additionally, the present invention is directed to a novel method of treating hypercholesterolemia or atherosclerosis comprising administering to a mammal in need of such treatment an acyl-coenzyme A:cholesterol acyltransferase-inhibitory effective amount of a compound of Formula I in unit dosage form.

Also, the present invention is directed to a pharmaceutical composition for treating hypercholesterolemia or atherosclerosis comprising an acyl-coenzyme A:-cholesterol acyl transferase-inhibitory effective amount of a compound of Formula I in combination with a pharmaceutically acceptable carrier.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to eight carbon atoms and includes, for example, methyl, ethyl, n-propyl, isopropyl, n-butyl, isobutyl, tertiary-butyl, n-pentyl, n-hexyl, n-heptyl, n-octyl, and the like.

"Alkoxy" is O-alkyl in which alkyl is as defined above.

Certain of the compounds of Formula I are capable of further forming pharmaceutically acceptable acid addition salts. Both of these forms are within the scope of the present invention. Pharmaceuticaly acceptable acid addition salts are formed with inorganic and organic acids, such as, for example, hydrochloric, sulfuric, phosphoric, acetic, citric, gluconic, fumaric, methanesulfonic, and the like (see, for example, Berge, S. M., et al, "Pharmaceutical Salts", *Journal of Pharmaceutical Science*, 66, pp. 1–19 (1977)). The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention. Certain of the compounds of the present invention possess asymmetric carbon atoms (optical centers), the racemates as well as the individual enantiomers are intended to be encompassed within the scope of the present invention.

A preferred compound of Formula I is one wherein $R_1$ hydrogen and $R_2$ is

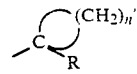

wherein n' is an integer of 2 to 6 and R is phenyl, phenyl mono or disubstituted with
alkyl of from one to four carbon atoms,
alkoxy of from one to four carbon atoms,
fluorine,
chlorine,
bromine,
iodine,
$CO_2R_3$ wherein $R_3$ is alkyl of from one to four carbon atoms, or
$NR_4 R_5$ wherein $R_3$ and $R_5$ are independently hydrogen or alkyl of from one to four carbon atoms, naphthyl, or naphthyl substituted with alkyl of from one to four carbon atoms,
alkoxy of from one to four carbon atoms,
fluorine,
chlorine,
bromine,
iodine,
$CO_2R_3$ wherein $R_3$ is as defined above, or
$NR_4R_5$ wherein $R_4$ and $R_5$ are as defined above,

where $R_6$ is hydrogen, alkyl of from one to eight carbon atoms or phenyl, $R_7$ is alkyl of from one to eight carbon atoms when $R_6$ is alkyl of from one to eight carbon atoms or $R_7$ is phenyl, and $R_8$ is phenyl or phenyl substituted with alkyl of from one to four carbon atoms, alkoxy of from one to four carbon atoms, fluorine, chlorine, bromine, iodine, $CO_2R_3$ wherein $R_3$ is as defined above, or $NR_4R_5$ wherein $R_4$ and $R_5$ are as defined above, or naphthyl.

Another preferred embodiment is a compound of Formula I wherein X is 0.

Particularly valuable are:

N-[2,6-Bis(1-methylethyl)phenyl]-N'-(diphenylmethoxy)-urea;

N-[2,6-Bis(1-methylethyl)phenyl]-N'-(triphenylmethoxy)-urea, and

N-2,6-Bis(1-methylethyl)phenyl]-N'-(1-naphthenylmethoxy)-urea; or a pharmaceutically acceptable acid addition salt thereof.

The compounds of the present invention are potent inhibitors of the enzyme acyl-CoA:cholesteryl acyltransferase (ACAT), and are thus effective in inhibiting the esterification and transport of cholesterol across the intestinal cell wall. Thus, the compounds of the present invention are useful in pharmaceutical formulations for the inhibition of intestinal absorption of dietary cholesterol, the reabsorption of cholesterol released into the intestine by normal body action, or the modulation of cholesterol.

The ability of representative compounds of the present invention to inhibit ACAT was measured using an in vitro test more fully described in Field, F. J. and Salome, R. G., *Biochimica et Biophysica Acta,* Volume 712, pages 557–570 (1982). The test assesses the ability of a test compound to inhibit the acylation of cholesterol by oleic acid by measuring the amount of radiolabeled cholesterol oleate formed from radio-labeled oleic acid in a tissue preparation containing rabbit intestinal microsomes. The data in Table I is expressed as $IC_{50}$ values, i.e., the concentration of test compound required to inhibit cholesteryl oleate formation to 50% of control. The data in the table shows the ability of representative compounds of the present invention to potently inhibit ACAT.

TABLE 1

| | Biological Activity of Compounds of Formula I | |
|---|---|---|
| Example Number | Compound | $IC_{50}$ ($\mu$ moles) |
| 1 | N-[2,6-Bis(1-methylethyl)phenyl]-N'-(diphenylmethoxy)-urea | 0.030 |
| 2 | N-[2,6-Bis(1-methylethyl)phenyl]-N'-(triphenylmethoxy)-urea | 0.053 |
| 3 | N-[2,6-Bis(1-methylethyl)phenyl]-N'-(1-naphthalenylmethoxy)-urea | 0.092 |

A compound of Formula I

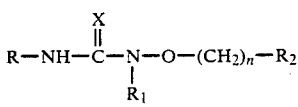

I wherein
R is phenyl,
phenyl mono or disubstituted with
  alkyl of from one to four carbon atoms,
  alkoxy of from one to four carbon atoms,
  fluorine,
  chlorine,
  bromine,
  iodine,
  $CO_2R_3$ wherein $R_3$ is alkyl of from one to four carbon atoms, or
  $NR_4R_5$ wherein $R_4$ and $R_5$ are independently hydrogen or alkyl of from one to four carbon atoms,
naphthyl, or
naphthyl substituted with alkyl of from one to four carbon atoms
  alkoxy of from one to four carbon atoms,
  fluorine,
  chlorine,
  bromine,
  iodine,
  $CO_2R_3$ wherein $R_3$ is as defined above, or
  $NR_4R_5$ wherein $R_4$ and $R_5$ are as defined above;
X is O or S;
$R_1$ is hydrogen,
alkyl of from four to eight carbon atoms, or phenylalkyl wherein alkyl is from one to four carbon atoms;
n is 0 or an integer of 1 or 2;
$R_2$ is bicyclo[2.2.1]heptane, bicyclo[2.2.2]octane,

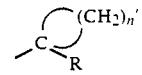

wherein n' is an integer of 2 to 6 and
  R is as defined above,

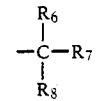

wherein $R_6$ is hydrogen, alkyl of from one to eight carbon atoms or phenyl, $R_7$ is alkyl of from one to eight carbon atoms when $R_6$ is alkyl of from one to eight carbon atoms or $R_7$ is phenyl, and $R_8$ is phenyl or phenyl substituted with alkyl of from one to four carbon atoms, alkoxy of from one to four carbon atoms, fluorine, chlorine, bromine, iodine, $CO_2R_3$ wherein $R_3$ is as defined above, or $NR_4R_5$ wherein $R_4$ and $R_5$ are as defined above,

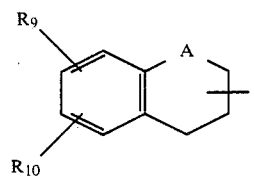

wherein $R_9$ and $R_{10}$ are independently hydrogen, alkyl of from one to four carbon atoms, alkoxy of from one to four carbon atoms, fluorine, chlorine, bromine, iodine, $CO_2R_3$ wherein $R_3$ is as defined above or $NR_4R_5$ wherein $R_4$ and $R_5$ are as defined above, and A is 0, S, SO, $SO_2$, or $-CH_2-$,
naphthyl or
naphthyl substituted with alkyl of from one to four
  carbon atoms,
  alkoxy of from one to four carbon atoms,
  fluorine,
  chlorine,
  bromine,
  iodine,
  $CO_2R_3$ wherein $R_3$ is as defined above, or
  $NR_4R_5$ wherein $R_4$ and $R_5$ are as defined above; or
  a pharmaceutically acceptable acid addition salt thereof is prepared by reacting a compound of Formula II

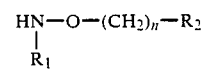

II wherein $R_1$, $R_2$, and n are as defined above with a compound of Formula III

R—N=C=X   III wherein R and X are as defined above in a solvent such as, for example, ethyl acetate and the like to give a compound of Formula I.

A compound of Formula IIb $$HN-O-(CH_2)_n-R_2 \quad \text{IIb}$$
$$|$$
$$R_{11}$$

wherein $R_{11}$ is alkyl of from four to eight carbon atoms or phenylalkyl wherein alkyl is from one to four carbon atoms and $R_2$ and n are as defined above, is prepared by reacting a compound of Formula IIa $$H_2N-O-(CH_2)_n-R_2 \quad \text{IIa}$$

wherein $R_2$ and n are as defined above with a compound of Formula IV $$R_{11}X \quad \text{IV}$$

wherein X is bromine or chlorine and $R_{11}$ is as defined above in the presence of a base such as, for example, sodium hydroxide, sodium carbonate, sodium bicarbonate, potassium hydroxide, potassium carbonate, potassium bicarbonate, and the like to give a compound of Formula IIb.

A compound of Formula IIa is either known or may be prepared using the methodology described by A. F. McKay, et al., *Canadian Journal of Chemistry*, Volume 38, pages 343–358 (1960), E. L. Schumann, et al, *Journal of Medicinal Chemistry*, Volume 7, pages 329–334 (1964), and P. Mamalis, et al, *Journal of the Chemical Society*, pages 229–238 (1960).

A compound of Formula III or Formula IV is either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included.

Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit dose containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 50 mg to 1500 mg preferably 200 mg to 500 mg according to the particular application and the potency of the active component. The composition can, if desired, also contain other compatible therapeutic agents.

The dosage range for a 70-kg mammal is from about 1 mg/kg to about 100 mg/kg of body weight per day or preferably about 3 mg/kg to about 15 mg/kg of body weight per day when the compounds of the present invention are used therapeutically as antihypercholesterolemic and antiatherosclerotic agents. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

N-[2,6-Bis(1-methylethyl)phenyl]-N'-(diphenylmethoxy)urea

To a solution of 1,1-diphenylmethoxyamine (0.9 g, 0.0045 mol) (E. L. Schumann, et al, *Journal of Medicinal Chemistry*, Volume 7, pages 329-334 (1964)) in 20 ml of ethyl acetate is added 2,6-diisopropylphenyl isocyanate (0.91 g, 0.0045 mol) and the reaction mixture is stirred for 20 hours at room temperature. The volatiles are removed under reduced pressure and the residue treated with 30 ml hexane-ethyl acetate (4:1). The precipitated solid is filtered and dried affording 1.45 g of N-[2,6-bis(1-methylethyl)phenyl]-N'-(diphenylmethoxy)-urea; mp 152°-154° C.

In a process analogous to Example 1 using appropriate starting materials, the corresponding compounds of Formula I are prepared:

EXAMPLE 2

N-[2,6-Bis(1-methylethyl)phenyl]-N'-(triphenylmethoxy)urea; mp 198°-200° C.

EXAMPLE 3

N-[2,6-Bis(1-methylethyl)phenyl]-N'-(1-naphthalenylmethoxy)-urea; mp 128°-130° C.

I claim:

1. A compound of Formula I

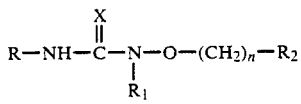

wherein
  R is phenyl,
    phenyl mono or disubstituted with
      alkyl of from one to four carbon atoms,
      alkoxy of from one to four carbon atoms,
      fluorine,
      chlorine,
      bromine,
      iodine,
      $CO_2R_3$ wherein $R_3$ is alkyl of from one to four carbon atoms, or
      $NR_4R_5$ wherein $R_4$ and $R_5$ are independently hydrogen or alkyl of from one to four carbon atoms,
    naphthyl, or
    naphthyl substituted with alkyl of from one to four carbon atoms
      alkoxy of from one to four carbon atoms,
      fluorine,
      chlorine,
      bromine,
      iodine,
      $CO_2R_3$ wherein $R_3$ is as defined above, or
      $NR_4R_5$ wherein $R_4$ and $R_5$ are as defined above;
  X is O or S;
  $R_1$ is hydrogen,
    alkyl of from four to eight carbon atoms, or
    phenylalkyl wherein alkyl is from one to four carbon atoms;
  n is 0 or an integer of 1 or 2;
  $R_2$ is bicyclo[2.2.1]heptane, bicyclo[2.2.2]octane,

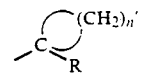

wherein n' is an integer of 2 to 6 and
R is as defined above,

wherein $R_6$ is hydrogen, alkyl of from one to eight carbon atoms or phenyl, $R_7$ is alkyl of from one to eight carbon atoms when $R_6$ is alkyl of from one to eight carbon atoms or $R_7$ is phenyl, and $R_8$ is phenyl or phenyl substituted with alkyl of from one to four carbon atoms, alkoxy of from one to four carbon atoms, fluorine, chlorine, bromine, iodine, $CO_2R_3$ wherein $R_3$ is as defined above, or $NR_4R_5$ wherein $R_4$ and $R_5$ are as defined above,

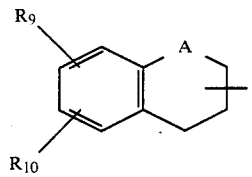

wherein $R_9$ and $R_{10}$ are independently hydrogen, alkyl of from one to four carbon atoms, alkoxy of from one to four carbon atoms, fluorine, chlorine, bromine, iodine, $CO_2R_3$ wherein $R_3$ is as defined above or $NR_4R_5$ wherein $R_4$ and $R_5$ are as defined above, and A is $-CH_2-$,
  naphthyl or
  naphthyl substituted with alkyl of from one to four carbon atoms,
    alkoxy of from one to four carbon atoms,
    fluorine,
    chlorine,
    bromine,
    iodine,
    $CO_2R_3$ wherein $R_3$ is as defined above or
    $NR_4R_5$ wherein $R_4$ and $R_5$ are as defined above;
    or a pharmaceutically acceptable acid addition salt thereof.

2. A compound as defined in claim 1 wherein $R_1$ is hydrogen and $R_2$ is

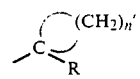

wherein n' is
  an integer of 2 to 6 and R is phenyl, phenyl mono or disubstituted with
    alkyl of from one to four carbon atoms,
    alkoxy of from one to four carbon atoms,
    fluorine,
    chlorine,
    bromine,
    iodine, CO₂R₃ wherein R₃ is alkyl of from one to four carbon atoms, or NR₄R₅ wherein R₄ and R₅ are independently hydrogen or alkyl of from one to four carbon atoms, naphthyl, or naphthyl substituted with alkyl of from one to four carbon atoms, alkoxy of from one to four carbon atoms, fluorine, chlorine, bromine, iodine, CO₂R₃ wherein R₃ is as defined above, or NR₄R₅ wherein R₄ and R₅ are as defined above,

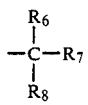

where R₆ is hydrogen, alkyl of from one to eight carbon atoms or phenyl, R₇ is alkyl of from one to eight carbon atoms when R₆ is alkyl of from one to eight carbon atoms or R₇ is phenyl, and R₈ is phenyl or phenyl substituted with alkyl of from one to four carbon atoms, alkoxy of from one to four carbon atoms, fluorine, chlorine, bromine, iodine, CO₂R₃ wherein R₃ is as defined above or NR₄R₅ wherein R₄ and R₅ are as defined above, or naphthyl.

3. A compound as defined in claim 2 wherein X is 0.

4. A compound as defined in claim 1 having the name N-[2,6-bis(1-methylethyl)phenyl]-N'-(diphenylmethoxy)-urea.

5. A compound as defined in claim 1 having the name N-[2,6-bis(1-methylethyl)phenyl]-N'-(triphenylmethyl)-urea.

6. A compound as defined in claim 1 having the name N-2,6-bis(1-methylethyl)phenyl]-N'-(1-naphthalenylmethoxy)-urea.

7. A method of treating hypercholesterolemia or atherosclerosis comprising administering to a mammal in need of such treatment an acylcoenzyme A: cholesterol acyltransferase-inhibitory effective amount of a compound as defined in claim 1 in unit dosage form.

8. A pharmaceutical composition for treating hypercholesterolemia or atherosclerosis comprising an acylcoenzyme A:cholesterol acyltransferase-inhibitory effective amount of a compound as defined in claim 1 in combination with a pharmaceutically acceptable carrier.

* * * * *